(12) United States Patent
Ben-Shachar et al.

(10) Patent No.: US 7,442,496 B2
(45) Date of Patent: Oct. 28, 2008

(54) METHODS AND KITS FOR DIAGNOSIS OF SCHIZOPHRENIA

(75) Inventors: Dorit Ben-Shachar, Kiryat Shmuel (IL); Ehud Klein, Timrat (IL)

(73) Assignee: Technion R&D Foundation Ltd. Business Development & Financial Control Dept., Haifa (IL)

( * ) Notice: Subject to any disclaimer, the term of this patent is extended or adjusted under 35 U.S.C. 154(b) by 659 days.

(21) Appl. No.: 10/432,354

(22) PCT Filed: Nov. 29, 2001

(86) PCT No.: PCT/IL01/01106

§ 371 (c)(1),
(2), (4) Date: May 29, 2003

(87) PCT Pub. No.: WO02/43559

PCT Pub. Date: Jun. 6, 2002

(65) Prior Publication Data

US 2004/0048236 A1 Mar. 11, 2004

Related U.S. Application Data

(60) Provisional application No. 60/253,927, filed on Nov. 30, 2000.

(51) Int. Cl.
C12Q 1/00 (2006.01)
C12Q 1/26 (2006.01)

(52) U.S. Cl. .............................. 435/4; 435/26

(58) Field of Classification Search ....................... None
See application file for complete search history.

(56) References Cited

OTHER PUBLICATIONS

Whatley et al. Superoxide, Neuroleptics and the Ubiquinone and Cytochrome B5 Reductases in Brain and Lymphocytes From Normals and Schizophrenic Patients; Molecular Psychiatry, vol. 3 (1998) pp. 227-237.*
McCormack et al. Influence or Calcium Ions on Mammalian Intramitochondrial Dehydrogenases; Methods in Enzymology, vol. 174 (1989) pp. 95-118.*
Aganova E. A., et al. "Morphometric Analysis of Synaptic Contacts in the Anterior Limbic Cortex in the Endogenous Psychoses" UDC 616.895.58-07:616,831.314-0918, 1992 Plenum Publishing Corporation.
Barbeau David, et al. "Decreased Expression of the Embryonic Form of the Neural Cell Adhesion Molecule in Schizophrenic Brains" Proc. Natl. Acad. Sci, vol. 92, pp. 2785-2789, Mar. 1995.
Ben-Shachar Dorit, et al. "Increased Mitochondrial Complex I Activity in Platelets of Schizophrenic Patients" International Journal of Neuropsychopharmacology (1992), 2, 245-253.
Be-Shachar Dorit, et al. "Dopamine Neurotoxicity: Inhibition of Mitochondrial Respiration" Journal of Neurochemistry, Raven Press Ltd, New York 1995, International Society for Neurochemistry.
Da Prada M, et al. "Platelets as a Model for Neurones?" Experientia 44 (1988).
Docherty, Nancy M. PhD et al, "Communication Disturbances in Schizophrenia and Mania", Arch Gen Psychiatry, 1996;53:358-364.
Dror, N., et al, "State-Dependent Alterations in Mitochondrial Complex I Activity in Platelets: A Potential Peripheral Marker for Schizophrenia", Molecular Psychiatry (2002) 7, 995-1001 Nature Publishing Group.
Estornell Ernesto et al. "Assay Conditions for the Mitochondrial NADH: Coenzyme Q Oxidoreductase" Federation of European Biochemical Societies vol. 332, No. 1,2, 127-131, 1993.
Ganguli Rohan, et al, "Autoimmunity in Schizophrenia: A Review o Frecent Findings" Annals of Medicine 25: 489-496, 1993.
Gavin Claire E. et al. "Manganese and Clacium Efflux Kinetics in Brain Mitochondria" Biochem J. (1990) 226, 329-334 vol. 266.
Gur Rachel E. et al. "Regional Brain Function in Schizophrenia" Arch Gen Psychiatry, vol. 44, Feb. 1987:44:126-129.
Harlow Ed, et al. "Antibodies—A Laboratory Manual" Cold Spring Harbor Laboratory 1988.
Hatefi Youssef "Introduction—Preparation and Properties of the Enzymes and Enzyme Complexes of the Mitochondrial Oxidative Phosphorylation System".
Hietala Jarmo et al. "Dopamine in Schizophrenia" Annals of Medicine 28: 557-561m 1996, The Finnish Medical Society.
Holcomb Henry H et al., "Functional Sites of Neuroleptic Drug Action in the Human Brain; PET/FDG Studies With and Without Haloperidol" Am J Psychiatry 153:1, Jan. 1996.
Kaiya H. et al., "Second Messenger Imbalance Hypothesis of Schizophrenia" Prostaglandins Leukotienes and Essential Fatty Acids (1992) 46, 33-38.
Meltzer H.Y. et al. "Clinical Services Research" Schizophrenia Bulletin, vol. 18, No. 4, 1992.
Krige David, et al. "Platelet Mitochondrial Function in Parkinson's Disease" American Neurological Association, 1992;32:782-788.

(Continued)

*Primary Examiner*—Jon P Weber
*Assistant Examiner*—Paul C. Martin
(74) *Attorney, Agent, or Firm*—Pearl Cohen Zedek Latzer, LLP

(57) ABSTRACT

The present invention provides methods and kits for the diagnosis of schizophrenia, which employ mitochondrial complex I as a peripheral biological marker for schizophrenia. In one embodiment, the present invention provides a method for diagnosing schizophrenia in a subject by determining the level of activity of a mitochondrial complex I enzyme in a sample obtained from the subject, and comparing the level of activity in the sample with a normative value of mitochondrial complex I enzyme activity, wherein an altered level of activity of mitochondrial complex I enzyme in the sample compared with the normative value is indicative of the subject having schizophrenia. In another embodiment, the present invention provides a method for diagnosing schizophrenia in a subject by determining the level of m-RNA or protein of mitochondrial complex I in a sample obtained from the subject, and comparing the level m-RNA or protein of mitochondrial complex I in the sample with a normative value of mitochondrial complex I m-RNA or protein, wherein an altered level of mitochondrial complex I m-RNA or protein in the sample compared with the normative value is indicative of the subject having schizophrenia. Kits for diagnosing schizophrenia using the methods of the present invention are also disclosed.

24 Claims, 2 Drawing Sheets

OTHER PUBLICATIONS

Kung Lili et al. "Mitochondiral Pathology in Human Schizophrenic Striatum: A Postmortem Ultrastuctural Studay" Synapse 31:67-75 (1999) Wilely-Liss, Inc.

McCormack James G. et al. "Influence of Calcium Ions on Mammalian Intramitochondrial Dehydrogenases" Methods in Enzymology, vol. 174 1989 Academic Press, Inc.

McGlashan Thomas H. "A Selective Review of Recent North American Long-Term Followup Studies of Schizophrenia" vol. 14, No. 4, 1988, Schizophrenia Bulletin.

McGlashan Thomas H. et al. "The Positive-Negative Distinciton in Schizophrenia" Arch Gen Psychiatry—vol. 49, Jan. 1992.

Moilanen, Kristiina et al, "Reasons for the Diagnostic Discordance Between Clinicians and Researchers in Schizophrenia in the Northern Finland 1966 Birth Cohort", Soc Psychiatry Psychiatr Epidemiol (2003) 38:305-310.

Parker William Davis Jr. et al. "Cytochrome Oxidase Deficiency in Alzheimer's Disease" Neurology 40, Aug. 1990; 40:1302-1303.

Pletscher A., "Platelets as Models: Use and Limitations", Experientia 44 (1988), Birkhauser Verlag., CH-4031 Basel (Switzerland).

Prince Jonathan A. et al., "Mitochondrial Function is Differentially Altered in the Basal Ganglia of Chronic Schizophrenics" Neuropsychopharmacology 1999, vol. 21, No. 3.

Przedborski Serge et al., "Chronic Levodopa Administration Alters Cerebral Mitochondrial Respiratory Chain Activity" American Neurological Association 1993;34:715-723.

Raedler, et al. "Schizophrenia as a Developmental Disorder of the Cerebral Cortex", Current Opinion in Neurobiology 1998, 8:157-161.

Ragan C.I. et. al, "Sub-Fractionation of Mitochondria and Isolation of the Proteins of Oxidative Phosphorylation".

Rosenthal, Robert E. et. al, "Cerebral Ischemia and Reperfusion: Prevention of Brain Mitochondrial Injury by Lodoflazine", Journal of Cerebral Blood Flow and Metabolism 7:752-758, 1987 Raven Press, Ltd., New York.

Schapira, A.H.V. et al., "Mitochondrial Complex I Deficiency in Parkinson's Disease", Journal of Neurochemistry, Raven Press, Ltd. New York, 1990 International Society for Neurochemistry.

Seeman, Philip, "Dopamine Receptors and the Dopamine Hypothesis of Schizophrenia", Synapse 1:133-152 (1987), Alan R Liss, Inc.

Tamminga, Carol A. MD, PhD; et. al., "Limbic System Abnormalities Identified in Schizophrenia Using Positron Emission Tomography With Fluorodeoxyglucose and Neocortical Alternations With Deficit Syndrome", Arch Gen Psychiatry-vol. 49, Jul. 1992.

Sheitman, Brian et al, "The Evaluation and Treatment of First-Episode Psychosis". Dorothea Dix Hosp, CRU-Edgerton Bldg, 809 Ruggles Dr., Raleigh, NC.

Singer, Thomas P. "Determination of the Activity of Succinate, Nadh, Choline, and A-Glycerophosphate Dehydrogenases", Dept. of Biochem and Biophys, Univ. of Cal, San Francisco & Molecular Biol. Div: Veterans Adm. Hosp, San Fran. California.

Storrie, Brian and Madden, Edward A. "Isolation of Subcellular Organelles", Methods of Enzymology, vol. 182, copyright 1990 by Academic Press.

Strunecka, A., and Ripova, D, Review "What Can the Investigation of Phosphoinositide Signaling System in Platelets of Schizophrenic Patients Tell Us?" Prostaglandins, Leukotrienes and Essential Fatty Acids (1999)61(1), 1-5 Harcourt Publishers Ltd.

Takahashi, Yasuo, "An Enzymological Study on Brain Tissue of Schizophrenic Patients★. Carbohydrate Metabolism. Part I. Glucose", Folia Psychiatrica et Neurologica, Japonica vol. 7, No. 3, 1953.

Tsuange, Ming T. MD, "Toward Reformulating the Diagnosis of Schizophrenia", Am J. Psychiatry 157:1041-1050, Jul. 2000.

Tsuange, Ming T. MD, PhD, "Suicide in Schizophrenics, Manics, Depressives, and Surgical Controls", Arch Gen Psychiatry-vol. 35, Feb. 1978.

Wesley Dingman C. et al. "Discriminating Characteristics of Suicides" Acta Psychiatr. Scand. 1986:74:91-97.

Whatley, S.A. et al. "Mitochondrial Involvement in Schizophrenia and Other Functional Psychoses", Neurochemical Research, vol. 21, No. 9, 1996, pp. 995-1004, Plenum Publishing Corp.

Whatley, SA et al, "Superoxide, Neuroleptics and the Ubiquinone and Cytochrome B5 Reductases in Brain and Lymphocytes From Normals and Schizophrenic Patients", Molecular Psychiatry (1998) 3, 227-237 Stockton Press.

Wyatt, R.J. et al, "An Economic Evaluation of Schizophrenia-1991", Soc Psychiatry Psychiatr Epidemiol (1995) 30:196-205, Springer-Verlag.

Yao, J.K. and Van Kammen, D.P., "Incorporation of 3H-Arachidonic Acid Into Platelet Phospholipids of Patients With Schizophrenia", Prostaglandins, Leukotrienes and Essential Fatty Acids (1996) 55(1 &2),21-26, Pearson Professional Ltd.

* cited by examiner

METHODS AND KITS FOR DIAGNOSIS OF SCHIZOPHRENIA

CROSS-REFERENCE

This application is a national phase of PCT International Application No. PCT/IL01/01106, International Filing Date Nov. 29, 2001, claiming priority of U.S. Provisional Application, 60/253,927 filed, Nov. 30, 2000.

FIELD OF THE INVENTION

The present invention generally relates to the field of disease diagnostics. More specifically, the present invention relates to a method for the diagnosis of schizophrenia.

BACKGROUND OF THE INVENTION

Schizophrenia is the most disabling psychiatric disorder, with a lifetime prevalence of about one-percent in the population (Bromet et al., 1974). Because schizophrenia usually appears early in life and is often chronic, the costs of the disorder are substantial. Schizophrenia accounts for about 2.5% of total direct health care expenditures and its costs reached about $16-$19 billion in the USA in 1990 (Wyatt et al., 1995). The indirect costs from factors such as loss of productivity and family burden was estimated at $46 billion (Wyatt et al., 1995; Attkisson et al., 1992). The disorder appears to be uniformly distributed worldwide, although pockets of high or low prevalence ma exist (Docherty et al., 1996). Unemployment rates can reach 70%-80% in severe cases, and it is estimated that schizophrenic patients constitute 10% of the totally and permanently disabled. Homelessness and schizophrenia have been linked, it has been estimated that about one-third of homeless single adults suffer from severe mental illness, largely schizophrenia.

The essential features of schizophrenia consist of a mixture of characteristic signs and symptoms that have been present for a significant length of time during a 1-month period, with some signs of the disorder persisting for at least 6 months (According to Diagnostic and Statistical Manual of Mental Disorder-IV, hereinafter DSM-IV). The symptoms involve multiple psychological processes, such as perception hallucinations), ideation, reality testing (delusions), thought processes (loose associations), feeling (flatness, inappropriate affect), behavior (catatonia, disorganization), attention, concentration, motivation (avolition, impaired intention and planning) and judgement. No single symptom is pathognomonic of schizophrenia. These psychological and behavioral characteristics are associated with a variety of impairments in occupational and social functioning. The disorder is noted for great heterogeneity across individuals and variability within individuals over time. It is also associated with an increased incidence of suicide, which occurs in up to 10% of patients (Dingman et al., 1986; Tsuang, 1978; McGlashan, 1988).

The characteristic symptoms of schizophrenia have often been conceptualized as falling into two broad categories—positive and negative (or deficit) symptoms—with a third category, disorganized, recently added. The positive symptoms include delusions and hallucinations. Disorganized symptoms include disorganized speech (Docherty et al., 1996), disorganized behavior and poor attention. Negative symptoms include restricted range and intensity of emotional expression (affective flattening), reduced thought and speech productivity (alogia), anhedonia, and decreased initiation of goal-directed behavior (avoliton) (McGlashan et al, 1992).

According to DSM-IV, subtypes of schizophrenia are defined by the predominant symptoms at the time of the most recent evaluation and therefore may change over time. These subtypes include 1) paranoid type, in which preoccupation with delusions or auditory hallucinations is prominent; 2) disorganized type, in which disorganized speech and behavior and flat or inappropriate affect are prominent; 3) catatonic type, in which the characteristic motor symptoms are prominent; 4) undifferentiated type, which is a nonspecific category used when none of the other subtype features is prominent; and 5) residual type, in which there is an absence of prominent positive symptoms but continuing evidence of disturbance (e.g., negative symptoms or positive symptoms in an attenuated form) (Barbeau et al, 1995).

The etiology of schizophrenia is still unknown. Recent advances in neuroscience and psychopharmacology have suggested a wide array of competing mechanisms that may be involved in schizophrenia, including a deficit in one or more neurotransmitters (e.g., dopamine, serotonin, GABA and glutamate), their second messengers (Kaiya, 1992; Yao et al., 1996; Strunecka et al., 1999), neurodevelopmental defects in brain (Raedler et al., 1998), and autoimmune mechanisms (Ganguli et al., 1993). Dopamine involvement in schizophrenia is still attracting considerable attention, despite the lack of direct evidence for abnormal dopaminergic function in the disorder. This is primarily based on the high correlation between the therapeutic efficacy of antipsychotic drugs and their potency as dopamine receptors blockers (Seeman, 1987), and the ability of dopamine agonists (such as bromrocriptine and L-DOPA) to induce acute psychotic symptoms with marked resemblance to schizophrenia. It has been suggested that acute psychotic episodes are associated with a hyperdopaminergic state in the mesolimbic regions, while negative symptoms are associated with a hypodopaminergic state in the mesocortical projections to the frontal cortex (Davis et al., 1991).

Symptoms of other mental disorders, especially depression but also obsessive and compulsive symptoms, somatic concerns, dissociative symptoms, and other mood or anxiety symptoms, are frequently seen with schizophrenia. The heterogeneity of the disorder and its comorbidity with symptoms of other mental disorders frequently renders schizophrenia difficult to diagnose. At present, definitive diagnosis of schizophrenia depends on descriptive behavioral and symptomatic information. Further, a very long time period, approximately 6 months, is required for the diagnosis of schizophrenia.

Since there is neither an effective biological marker for identifying schizophrenia (Willner, 1997; Hietala, et al., 1996), nor an accurate and rapid diagnosis for more optimal management of the disease at its different stages (Sheitman et al., 1997), there remains an essential need for a reliable biological assay for the diagnosis and follow-up of schizophrenia. Identifying a peripheral biological marker will provide a) a more precise diagnosis and prognosis and might even shorten the 6-month period needed for diagnosis of schizophrenia; b) the possibility of using the peripheral marker as an objective tool for the patient's compliance to medication, if the marker responds differently in the presence of different types of antipsychotics; and c) a correlation between the candidate marker and any feature of schizophrenia will contribute to the knowledge of the basic pathophysiology of the disorder, which might lead to new therapeutic strategies more specific and with fewer side effects.

SUMMARY OF THE INVENTION

The present invention provides a method for diagnosing schizophrenia in a subject, comprising the steps of obtaining a sample from the subject, determining the level of activity of a mitochondrial complex I enzyme in the sample, and comparing the level of activity with a normative value of activity of mitochondrial complex I enzyme, wherein an altered level of activity of mitochondrial complex I enzyme in the sample compared with the normative value is indicative of the subject having schizophrenia.

In one embodiment, the sample is a blood sample, for example a platelet, lymphocyte, leukocyte, monocyte, or T-cell, B-cell or neutrophil blood sample. In another embodiment, the blood sample is a platelet sample that is enriched for mitochondria.

In one embodiment, a higher level of activity of mitochondrial complex I enzyme in the sample from the subject compared with the normative value is indicative of the subject having schizophrenia at an acute phase or a residual phase with pronounced positive symptoms, as defined herein. In another embodiment, a lower level of activity of mitochondrial complex I enzyme in the sample from the subject compared with the normative value is indicative of the subject having schizophrenia at a residual phase with pronounced negative symptoms, as defied herein.

In one embodiment, the mitochondrial complex I enzyme is NADH dehydrogenase. The level of activity of NADH dehydrogenase is determined by adding a portion of the sample to a medium containing an electron acceptor and NADH, and monitoring the change in absorbance of NADH. In one embodiment, the electron acceptor is ubiquinone. In another embodiment, the electron acceptor is ferricyanide.

The present invention further provides a method for diagnosing schizophrenia in a subject, comprising the steps of obtaining a sample from the subject, aliquoting a first test sample and a second test sample from the sample, adding a mitochondrial complex I enzyme inhibitor to the second test sample, determining the level of activity of a mitochondrial complex I enzyme in the first test sample and in the second test sample, determining the inhibition of the mitochondrial complex I enzyme in the second sample, and comparing the inhibition with a normative value of inhibition of the mitochondrial complex I enzyme, wherein an altered inhibition of mitochondrial complex I enzyme in the sample compared with the normative value is indicative of the subject having schizophrenia.

In one embodiment, the inhibitor is a catechol, for example dopamine, norepinephrine, 6-hydroxydopamine, L-DOPA or any combination thereof.

In one embodiment, the sample is a blood sample, for example a platelet, lymphocyte, leukocyte, monocyte, or T-cell, B-cell or neutrophil blood sample. In another embodiment, the blood sample is a platelet sample that is enriched for mitochondria.

In one embodiment, a higher inhibition of a mitochondrial complex I enzyme in the sample from the subject compared with the normative value is indicative of the subject having schizophrenia.

In one embodiment the mitochondrial complex I enzyme is NADH dehydrogenase. The level of activity of NADH dehydrogenase is determined by adding a portion of the sample to a medium containing an electron acceptor and NADH, and monitoring the change in absorbance of NADH. In one embodiment, the electron acceptor is ubiquinone. In another embodiment, the electron acceptor is ferricyanide.

The present invention further provides a method for diagnosing schizophrenia in a subject, comprising the steps of obtaining a sample from the subject, determining the level of m-RNA or protein of mitochondrial complex I in the sample, and comparing the level of m-RNA or protein of mitochondrial complex I in the sample with a normative value of mitochondrial complex I m-RNA or protein, wherein an altered level of m-RNA or protein of mitochondrial complex I in the sample from the subject compared with the normative value is indicative of the subject having schizophrenia.

In one embodiment, the sample is a blood sample, for example a platelet, lymphocyte, leukocyte, monocyte, or T-cell, B-cell or neutrophil blood sample. In another embodiment, the blood sample is a platelet sample that is enriched for mitochondria.

In one embodiment, the level of m-RNA of mitochondrial complex I is determined by measuring the level of m-RNA of a subunit of mitochondrial complex I. In another embodiment, the level of protein of mitochondrial complex I is determined by measuring the level of protein of a subunit of mitochondrial complex I.

In one embodiment, a higher level of m-RNA or protein of the subunit of mitochondrial complex I in the sample from the subject compared with the normative value is indicative of the subject having schizophrenia.

In one embodiment, the mitochondrial complex I subunit is a 24 kDa subunit. In another embodiment, the mitochondrial complex I subunit is a 51 kDa subunit.

In one embodiment, the level of m-RNA of the subunit of mitochondrial complex I is determined by isolating RNA from the sample, contacting the RNA with primers which are specific for the subunit of mitochondrial complex I, performing RT-PCR on the sample, and determining the level of m-RNA of the subunit of mitochondrial complex I.

In one embodiment, the level of protein of the subunit of mitochondrial complex I is determined by contacting the sample with a binding protein which specifically binds to the subunit of mitochondrial complex I, and detecting the amount of binding protein bound to the subunit of mitochondrial complex I. In one embodiment, the binding protein is an antibody. The antibody is a polyclonal antibody, a monoclonal antibody or a recombinant antibody. In one embodiment, the binding protein is labeled with a detectable label, which can be an enzyme, a fluorophore, a chromophore, a radioisotope, a dye, a bioluminescent agent or a chemiluminescent agent.

The present invention further provides a kit for diagnosing schizophrenia in a subject comprising a container for containing a sample from the subject, at least one reagent for determining the level of activity of a mitochondrial complex I enzyme, and at least one buffer or solution.

In one embodiment, the reagent is for determining the activity of NADH dehydrogenase. In one embodiment, there are at least two reagents, including NADH and an electron acceptor. In one embodiment, the electron acceptor is ferricyanide. In another embodiment, the electron acceptor is ubiquinone.

In one embodiment, the kit further comprises a mitochondrial complex I inhibitor, which can be a catechol, for example dopamine, 6-hydroxydopamine, L-DOPA, norephinephrine or any combination thereof.

The present invention further provides a kit for diagnosing schizophrenia in a subject comprising a container for containing a sample from the subject, at least one reagent for determining the level of m-RNA or protein of mitochondrial complex I, and at least one buffer or solution.

In one embodiment, the reagent is for determining the m-RNA level or protein level of a subunit of mitochondrial complex I. In one embodiment, the subunit is a 24 kDa subunit. In another embodiment, the subunit is a 51 kDa subunit.

In one embodiment, the reagent is for determining the m-RNA level of a subunit of mitochondrial complex I. The reagent comprises at least one reagent and buffer for isolating RNA from said sample, at least two primers which are specific for the subunit of mitochondrial complex I, and reagents and buffers for an RT-PCR assay.

In one embodiment, the reagent is for determining the protein level of a subunit of mitochondrial complex I. The reagent comprises a binding protein, which specifically binds to the subunit of mitochondrial complex I. In one embodiment, the binding protein is an antibody. The antibody is a polyclonal antibody, a monoclonal antibody or a recombinant antibody. In one embodiment, the binding protein is labeled with a detectable label. The label is an enzyme, a fluorophore, a chromophore, a radioisotope, a dye, a bioluminescent agent or a chemiluminescent agent.

BRIEF DESCRIPTION OF THE DRAWINGS

The present invention will be understood and appreciated more fully from the following detailed description taken in conjunction with the appended drawings in which:

FIG. 3A shows m-RNA levels of the 24 kDa subunit of complex I; FIG. 3B shows m-RNA levels of the 51 kDa subunit of complex I; FIG. 3C shows m-RNA levels of the 75 kDa subunit of complex I; and FIG. 3D shows m-RNA levels of beta actin.

DETAILED DESCRIPTION OF THE INVENTION

Figure 1:
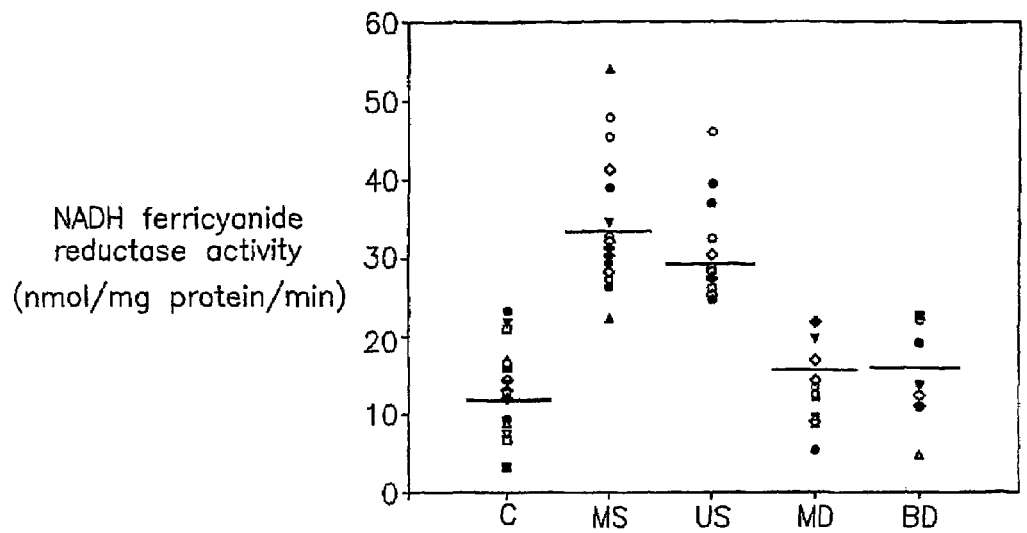
FIG. 1: depicts individual values of NADH ferricyanide reductase activity in medicated (MS) and unmedicated (US) schizophrenic patients, patients with major depression (MD), patients with bipolar disorder (BP), and control subjects (C).

The present invention provides methods and kits for the diagnosis of schizophrenia, which employ mitochondrial complex I as a peripheral biological marker for schizophrenia. The identification of mitochondrial complex I as a biological marker 1) provides a reliable and rapid biological assay for the diagnosis and follow-up of schizophrenia that may shorten the 6-month period currently needed for the diagnosis of schizophrenia; 2) contributes to the knowledge of the basic pathophysiology of the disease, which might lead to new therapeutic strategies, and 3) permits the mitochondrial complex I to be a target gene for this multi-gene disorder.

As demonstrated herein, mitochondrial complex I activity is significantly altered in platelets of schizophrenic patients compared with control subjects. Patients with affective disorders such as major depression and bipolar disorder, by contrast, show a similar mitochondrial complex I activity as control subjects. Further, the levels of m-RNA and protein of mitochondrial complex I are significantly altered in platelets of schizophrenic patients compared with control subjects.

Thus, the present invention provides methods and kits for diagnosing schizophrenia by determining the level of activity of a mitochondrial complex I enzyme in a subject and comparing the activity with a normative value of activity of the mitochondrial complex I enzyme. The present invention further provides methods and kits for diagnosing schizophrenia by determining the level of m-RNA or protein of complex I in a subject and comparing the level of m-RNA or protein with a normative level of m-RNA or protein of mitochondrial complex I.

For the purposes of this invention, schizophrenic patients are broadly categorized as a function of their clinical state as being in an acute phase or in a residual (chronic) phase. Patients in acute phase experience acute relapse or are in acute psychotic exacerbation. Patients in residual phase are patients whose condition is stable (chronic). Residual patients are divided into two groups: 1) patients with pronounced positive symptoms (chronic active); and 2) patients without pronounced positive symptoms who experience mainly negative symptoms. Positive symptoms include delusions and hallucinations. Negative symptoms include restricted range and intensity of emotional expression (affective flattening), reduced thought and speech productivity (alogia), anhedonia, and decreased initiation of goal-directed behavior (avolition). For the purpose of this invention, a schizophrenic subject can be in any one of the clinical states defied above.

Applicant has determined that mitochondrial complex I is altered in schizophrenic patients when compared with a normative value of mitochondrial complex I. A "normative value" means a value reflective of a normal mitochondrial complex I level of a control subject who does not have schizophrenia.

In one embodiment of the present invention, mitochondrial complex I is assayed by determining the level of activity of a mitochondrial complex I enzyme. Thus, the present invention provides a method for diagnosing schizophrenia in a subject by determining the level of activity of a mitochondrial complex I enzyme in a sample obtained from the subject, and comparing the level of activity in the sample with a normative value of mitochondrial complex I enzyme activity. An altered level activity of mitochondrial complex I enzyme compared with the normative value is indicative of the subject having schizophrenia.

The sample can be any sample that contains mitochondrial complex I, for example a tissue sample. Suitable samples may be obtained from a veterinary or human patient and include, but are not limited to, whole blood cells, any mononuclear cell, leukocytes, lymphocytes, T-cells, B-cells, monocytes, platelets, megakaryocytes, neutrophils, eosinophils, basophils or peripheral blood mononuclear cells.

In one embodiment, the blood sample is enriched for mitochondria. General methods for isolation of mitochondria are disclosed in Ben-Schachar et al (1995), Gavin et al (1990), Rosenthal et al (1987) and McComark and Denton (1989) and described in detail in the examples that follow. The advantage of studying mitochondrial respiration lies in the fact that mitochondria are partly independent organelles, contain their own DNA and are highly preserved along evolution and in different tissues.

In one embodiment, the blood sample is a blood platelet sample. Platelets have been traditionally used as a peripheral model that may reflect brain changes in several neuropsychiatric disorders. Numerous studies have shown that platelets from schizophrenic patients behave differently than those isolated from healthy controls in dopamine uptake, 5-HT content, arachidonic acid metabolism, inositol phosphate levels and disturbance of calcium homeostasis (Kaiya, 1992; Yao et al., 1996; Strunecka et al., 1999). A correlation between biochemical changes in brain and platelets was also reported. For example, a reduction in imipramine binding was found both in platelets and in postmortem brains of deceased depressed patients and patients who committed suicide (Wirz-Justce, 1988). In patients with Parkinson's or Alzheimer's diseases, a correlation has been demonstrated between platelet and postmortem brains for the reduction in mitochondrial complex I and cytochrome c oxidase activities, respectively (Parker et al., 1990; Schapira et al., 1990). In additions biochemical and pharmacological similarities exist between blood platelets and 5HT or DA containing neurons of the CNS (Da Prada et al., 1988).

In one embodiment, the mitochondrial complex I enzyme is a mitochondrial enzyme respiratory chain enzyme. In one embodiment, the enzyme is NADH dehydrogenase. NADH dehydrogenase activity cart be measured using well-known assays, such as the assays described in Singer et al. (1974); Estronell (1993); Hatefi (1978); Ragan et al. (1987), and Ben Schachar et al. (1999). Briefly, NADH dehydrogenase activity is measured using an electron acceptor. In one embodiment, the electron acceptor is a biological electron acceptor, such as ubiquinone. In another embodiment, the electron acceptor is an artificial electron acceptor, such as ferricyanide, for example potassium ferricyanide. The assay comprises incubating a sample obtained from a subject with NADH and the electron acceptor, and measuring the change in absorbance of NADH at 340 nm over time.

The alteration in the level of activity of the mitochondrial complex I enzyme is dependent on the state of the disease. For example, Applicant has demonstrated a significant increase in mitochondrial complex I activity in mitochondria from platelets of medicated and unmedicated patients at acute exacerbation compared to control subjects, as discussed in detail in the examples below. Furthermore, Applicant has demonstrated a significant increase in mitochondrial complex I activity in mitochondria from platelets of residual patients with positive symptoms compared to control subjects, as discussed in detail in the examples below. On the other hand, Applicant has demonstrated a decrease in mitochondrial complex I activity in mitochondria from platelets of residual patients with negative symptoms compared to control subjects, as discussed in detail in the examples below. No difference in enzyme activity was observed between depressed patients with recurrent major depression or bipolar disorder and control subjects.

Other respiratory chain enzymes of mitochondrial complex I are the cytochrome b-cl complex and the cytochrome c oxidase complex. The level of activity of cytochrome c oxidase is not altered in schizophrenic patients compared to control subjects, as discussed in detail in the examples below.

In addition, in accordance with another embodiment of the present invention, the level of activity of a mitochondrial complex I enzyme is assayed in the presence or absence of a mitochondrial complex I inhibitor. Thus, the present invention provides a method for diagnosing schizophrenia in a subject by determining the inhibition of a mitochondrial complex I enzyme by a mitochondrial complex I enzyme inhibitor, and comparing the inhibition with a normative value of inhibition of the mitochondrial complex I enzyme, wherein an altered inhibition of the mitochondrial complex I enzyme compared with the normative value is indicative of the subject having schizophrenia.

Inhibitors of mitochondrial complex I enzyme activity are catechols, such as for example dopamine, 6-hydroxydopamine, L-DOPA and norepinephrine (Been-Schachar et al, 1995). Applicant and others have shown that catechols, primarily dopamine, can inhibit mitochondrial respiration by interfering with complex I both in vivo and in vitro (Ben-Schachar, 1995; Cohen, 1997; Przedborski et al., 1993 and unpublished data).

Applicant has found that the inhibition of mitochondrial complex I enzyme by dopamine is altered in some schizophrenic patients compared with a normative value of inhibition in control subjects. For example, Applicant has demonstrated a significant increase in inhibition of complex I activity by dopamine in mitochondria from platelets of schizophrenic patients in acute exacerbation compared to control subjects, as discussed in detail in the examples below. On the other hand, a similar level of inhibition of mitochondrial complex I activity in mitochondria from platelets of patients with recurrent major depression and patients with bipolar disorder compared to control subjects was observed, as discussed in detail in the examples below.

In accordance with yet another embodiment of the present invention, mitochondrial complex I is assayed by measuring the level of m-RNA or protein of the complex. Thus, the present invention provides a method for diagnosing schizophrenia in a subject by determining the level of m-RNA or protein of mitochondrial complex I in a sample obtained from the subject, and comparing the level of m-RNA or protein of mitochondrial complex I in the sample with a normative value of mitochondrial complex I m-RNA or protein. An altered level of mitochondrial complex I m-RNA or protein in the sample from the subject as compared to the normative value is indicative of the subject having schizophrenia.

In operation, the level of m-RNA or protein of mitochondrial complex I is determined by determining the level of m-RNA or protein of a subunit of mitochondrial complex I. Mitochondrial complex I is constituted from about 42 polypeptides, some of which are encoded by the nuclear DNA and others by mitochondrial DNA. For the purpose of this invention, any of the subunits may be studied. For example, in one embodiment, subunits that are encoded by the nuclear DNA may be studied.

Examples of subunits of mitochondrial complex I are: 1) 24- and 51 kDa subunits, which are iron-sulfur flavoprotein, which have catalytic properties including the site for transhydrogenation from NADH to NAD+; and 2) the 75 kDa subunit, the largest iron-sulfur protein, which demonstrates no catalytic activity. Applicant has found that the level of m-RNA and protein of the 24 and 51 kDa subunits significantly increases in schizophrenic patients compared with control subjects. In contrast, no change was found in the 75 kDa submit, as discussed in detail in the examples below.

m-RNA levels can be determined according to standard techniques, using reverse transcriptase polymerase chain reaction (RT-PCR) technology. RT-PCR technology is generally described in *PCR Protocols: A Guide to Methods and Applications*, (Academic Press, San Diego, Calif., 1990). Reactions and manipulations involving other nucleic acid techniques are described in Sambrook et al., *Molecular Cloning: A Laboratory Manual*, (Cold Springs Harbor Laboratory Press).

Protein levels can be determined according to standard techniques, as described in Sambrook et al. Briefly, a sample obtained from a subject is contacted with a binding protein which specifically binds to a subunit of mitochondrial complex I, and the amount of complex formed between the binding protein and the subunit of mitochondrial complex I is determined.

In one embodiment, the binding protein is an antibody which specifically, binds to a subunit of mitochondrial complex I. In another embodiment, the binding protein is an antibody which specifically binds to the 24 kDa subunit of mitochondrial complex I. In another embodiment, the binding protein is an antibody which specifically binds to the 51 kDa subunit of mitochondrial complex I.

In one embodiment, the binding protein has a detectable label bound thereto, and the complex between the binding protein-label and the subunit of mitochondrial complex I is determined by visualizing the complex.

As defined herein, "contacting" means that the binding protein is introduced into the sample in a test tube, flask, tissue culture, chip, array, plate, microplate, capillary, or the like, and incubated at a temperature and time sufficient to permit the binding component to bind to a cell or a fraction thereof or plasma/serum or a fraction thereof containing the target. Methods for contacting the samples with the binding proteins, or other specific binding components are known to those skilled in the art and may be selected depending on the type of assay protocol to be run. Incubation methods are also standard and are known to those skilled in the art.

"Visualizing" the complex of label and binding protein of each of the subunits of mitochondrial complex I may be carried out by any means known in the art, including, but not limited to, ELISA, radioimmunoassay, flow cytometry, dot blots, western immunoblotting combined with gel electrophoresis, immunohistochemistry, HPLC and mass spectrometry.

"Specifically binds to", when referring to a protein or peptide, refers to a binding reaction which is determinative of the presence of a subunit of mitochondrial complex I in the presence of a heterogeneous population of proteins and other biologics other than said subunit. Thus, the immunoassay conditions, the specified antibodies bind to the specific mitochondrial complex I subunit antigen and do not bind in a significant amount to other antigens present in the sample. Specific, binding to an antibody under such conditions may requite an antibody that is selected for its specificity for a particular protein. For example, antibodies raised to the human mitochondrial complex I 24 kDa subunit immunogen described herein can be selected to obtain antibodies specifically immunoreactive with the mitochondrial complex I 24 kDa subunit proteins and not with other proteins. In another example, antibodies raised to the human mitochondrial complex I 51 kDa subunit immunogen described herein can be selected to obtain antibodies specifically immunoreactive with the mitochondrial complex I 51 kDa subunit proteins and not with other proteins. One can use immunoassays to detect for the complex formed between the binding protein and the subunit of mitochondrial complex I. A general overview of the applicable technology is in Harlow and Lane (1988). Furthermore, a description of general immunometric assays of various types can be found in U.S. Pat. No. 4,376,110 (David et al.) or U.S. Pat. No. 4,098,876 (Piasio).

Specifically, detection and quantification include but are not limited to precipitation of the protein containing the biomarker by an antibody which binds to the biomarker; competitive immunoassays; Western immunoblotting in which the biomarker (either as part of mixture or contained in an immunoprecipitated complex) is separated by gel electrophoresis, transferred to a suitable support (e.g. nitrocellulose) and visualized by reaction with an antibody(ies); radioimmunoassay, in which the degree to which the protein competes with a radioactively labeled standard for binding to the antibody is used as a means of detecting and quantifying the protein; and enzyme-linked immuno-sorbant assay (ELISA).

ELISA is a known technique for quantifying proteins in which, for quantifying proteins in which, an antibody against the protein of interest is immobilized on an inert solid, e.g., polystyrene. A sample to be assayed for the protein of interest is applied to the surface containing immobilized antibody. Protein binds the antibody, forming a complex. This complex is then contacted by a second antibody which binds the same protein and which is covalently bound to an easily assayed enzyme. After washing away any of the second antibody which is unbound, the enzyme in the immobilized complex is assayed, providing a measurement of the amount of protein in the sample. The ELISA procedure can be reversed, i.e., the antigen is immobilized on an inert support (e.g. 96-well microplate) and samples are probed for the presence of antibody to the immobilized antigen. The biomarker can also be detected and its localization determined in cells and tissues using immunohistochemical procedures.

Further, cells may be detected using standard flow cytometry analysis using FACscan analyzer (Becton Dickinson, San Jose, Calif.). Cytometric techniques are known to those skilled in the art. For example the following describe such techniques and are hereby incorporated by reference in their entirety; U.S. Pat. No. 5,298,426 Method of differentiating erythroblasts from other cells by flow cytometry; U.S. Pat. No. 5,296,378 Method for classifying leukocytes by flow cytometry; U.S. Pat. No. 5,270,548 Phase-sensitive flow cytometer; U.S. Pat. No. 5,247,340 Flow imaging cytometer; U.S. Pat. No. 5,179,026 Method of classifying leukocytes by flow cytometry. Reagents used in the cytometric method include and are hereby incorporated by reference in their entirety: U.S. Pat. No. 5,175,109 Reagent for classifying leukocytes by flow cytometry; U.S. Pat. No. 5,167,926 Apparatus for pretreating cells for flow cytometry; U.S. Pat. No. 5,160,974 Closed sample cell for use in flow cytometry; U.S. Pat. No. 5,159,403 Flow cell mechanism in flow imaging cytometer; U.S. Pat. No. 5,159,398. Flow imaging cytometer; U.S. Pat. No. 5,150,313 Parallel pulse processing and data acquisition for high speed, low error flow cytometry; U.S. Pat. No. 5,144,224 Millimeter wave flow cytometer; U.S. Pat. No. 5,093,234 Method of aligning, compensating, and calibrating a flow cytometer for analysis of samples, and microbead standards kit therefor; U.S. Pat. No. 5,073,497 Microbead reference standard and method of adjusting a flow cytometer to obtain reproducible results using the microbeads U.S. Pat. No. 5,039,613 Reagents used in a method of classifying leukocytes cytometry U.S. Pat. No. 5,032,381 Chemiluminescence-based static and flow cytometry; and U.S. Pat. No. 4,954,715 Method and apparatus for an optimized multiparameter.

In one embodiment, western blotting is a method of detection of the mitochondrial complex I subunit that is suitable for the present invention.

Either monoclonal or polyclonal antibodies (as well as any recombinant antibodies) specific for the subunit of mitochondrial complex I can be used in the various immunoassays. Polyclonal antibodies against peptides of a specific subunit of mitochondrial complex I may be produced by immunizing animals using the selected peptides. Alternatively, monoclonal antibodies may be produced by in vitro techniques known to a person of ordinary skill in the art. For example, monoclonal antibodies are prepared using hybridoma technology by fusing antibody producing B cells from immunized animals with myeloma cells and selecting the resulting hybridoma cell line producing the desired antibody. The antibodies directed to the subunits of mitochondrial complex I may be coupled to a solid-phase support e.g., nitrocellulose, nylon, column packing materials (e.g., Sepharose beads), magnetic beads, on a chip, array, glass wool, plastic, metal, polymer gels, cells, or other substrates. Such supports may take the form, for example, of beads, wells, dipsticks, or membranes. The antibodies may be detectably labeled, utilizing conventional labeling techniques well-known to the art. As used herein, the term "label" refers to a molecule, which may be conjugated or otherwise attached (i.e., covalently or non-covalently) to a binding protein as defined herein. Labels are known to those skilled in the art. Thus, the antibodies may be labeled with radioactive isotopes, non-radioactive isotopic labels, fluorescent labels, enzyme labels, chemiluminescent labels, bioluminescent labels, free radical labels, or bacteriophage labels, using techniques known in the art. Examples of radioisotopic labels are $^3$H, sup.125 I, $^{131}$I, $^{35}$S, $^{14}$C, etc. Examples of non-radioactive isotopic labels are $^{55}$Mn, $^{56}$Fe, etc.

Examples of fluorescence labels are fluorescent labels which are directly labeled with a fluorescence label, or fluorescent labels which are indirectly labeled with a fluorescence label. In the last case, the fluorescence label is conjugated to a secondary antibody, which is directed against the first antibody, such as an anti species Ig antibody. Typical fluorescent labels include, but are not limited to a fluorescein label, an isothiocyanate label, a rhodamine label, a phycoerythrin label, etc., for example fluorescein isothiocyanate (FITC, International Biological Supplies, Melbourne, Fla.), rhodamine, phycoerythrin (P.E., Coulter Corp., Hialeah, Fla.), phycocyanin alophycocyanin, phycoerythrin-cyanin dye 5 (PECy5, Coulter), label, a phycocyanin label, an allophycocyanin label, an O-phthaldehyde label, a fluorescamine and Texas Red.

Examples of enzyme labels include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Particularly suitable labels include those, which permit analysis by flow cytometry, e.g., fluorochromes. Other suitable detectable labels include those useful in colorimetric enzyme systems, e.g., horseradish peroxidase (HRP) and alkaline phosphatase (AP). Other proximal enzyme systems are known to those of skill in the art, including hexokinase in conjunction with glucose-6-phosphate dehydrogenase.

Additionally, chemiluminescent compounds may be used as labels. Chemiluminescent labels, such as green fluorescent proteins, blue fluorescent proteins, and variants thereof are known. Also bioluminescence or chemiluminescence can be detected using, respectively, NAD oxidoreductase with luciferase and substrates NADH and FNIN or peroxidase with luminol and substrate peroxide. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin. Once labeled, the antibody may be employed to identify and quantify immunologic counterparts (antibody or antigenic polypeptide) utilizing techniques well-known to the art.

In a further embodiment of this invention, commercial test kits are disclosed which are suitable for use to determine the level of activity and/or level or m-RNA and/or level of protein of mitochondrial complex I, in order to diagnose whether a subject has schizophrenia.

In accordance with the testing techniques discussed above, one class of such kits will contain a container for containing a sample from the subject, at least one reagent for determining the level of activity of a mitochondrial complex I enzyme; and at least one buffer or solution. The container may be any container which can contain the sample, such as vial, tube, flask, box, bottle and the like.

The activity of mitochondrial complex I enzyme is determined using any of the methods described hereinabove. For example, when the activity of mitochondrial complex I is determined by monitoring the activity of NADH dehydrogenase, the kit comprises reagents for determining the activity of NADH dehydrogenase, such as NADH and an electron acceptor. In one embodiment, the electron acceptor is a biological electron acceptor, such as ubiquinone. In another embodiment, the electron acceptor is an artificial electron acceptor, such as ferricyanide, for example potassium ferricyanide. Other reagents, buffers and solutions for an NADH dehydrogenase assay are disclosed in Singer et al. (1974); Estornell (1993); Hatefi (1978); and Ragam (1987) and described in detail in the examples below. The kit may also contain peripheral reagents such as buffers, stabilizers, etc.

In accordance with the testing techniques discussed above, another class of such kits will contain a container for containing a sample from the subject, at least one reagent for determining the level of m-RNA or protein of mitochondrial complex I, and at least one buffer or solution.

Reagents for determining the level of m-RNA of mitochondrial complex I include specific primers for a subunit of mitochondrial complex I. For example, in one embodiment, the kit includes 5' and 3' primers for the 24 kDa subunit of mitochondrial complex I. In another embodiment, the kit includes 5' and 3' primers for the 51 kDa subunit of mitochondrial complex I. Other reagents used are standard reagents, buffers and solutions for RT-PCR reactions, such as described in PCR Protocols: A Guide to Methods and Application, (Academic Press, San Diego, Calif., 1990). Suitable reagents for determining the level of protein of mitochondrial complex I includes antibodies that specifically bind to a subunit of mitochondrial complex I. For example, in one embodiment, the kit comprises an antibody that binds to the 24 kDa subunit of mitochondrial complex I. In another embodiment, the kit comprises an antibody that binds to the 51 kDa subunit of mitochondrial complex I. The antibodies maybe labeled to enable detection, as described above. Detection of antibodies is done by standard techniques, as described in Sambrook et al., *Molecular cloning: A laboratory Manual* Cold Springs Harbor Laboratory Press).

The above discussion provides a factual basis for the use of mitochondrial complex I as a biological marker in the diagnosis of schizophrenia. The methods used with and the utility of the present invention can be shown by the following non-limiting examples and accompanying figures. This section is set forth to aid in an understanding of the invention but is not intended and should not be construed to limit in any way the invention as set forth in the claims that follow thereafter.

EXAMPLES

Example 1

Determination of Mitochondrial Complex I Activity in Schizophrenic Patients, Patients with Affective Disorders and Normal Subjects Complex I activity was determined by measuring NADH ferricyanide reductase activity or NADH ubiquinone reductase activity in medicated and unmedicated schizophrenic patients, patients with recurrent major depression, patients with bipolar disorder, the depressed type and healthy controls (Ben-Schachar et al, 1999).

Materials and Methods

Subjects

A total of 77 inpatients and 24 control subjects participated in the study. All patients met DSM-IV criteria for schizophrenia (acute exacerbation), bipolar disorder (BD) depressed type, or recurrent major depression (MDD). Consensus diagnosis by two senior psychiatrists was based on extended clinical interviews and reviews of patients' charts. Patients with schizoaffective illness were excluded. Twenty-four subjects without prior psychiatric history served as a control group. This group was age and sex matched to the schizophrenic group. Table 1 displays' some of the demographic characteristics of the study groups. All schizophrenic patients (n=50) were in a state of acute psychotic exacerbation. At the time of blood sampling, 25 had been medication-free for at least one month and most patients had not received medication for significantly longer periods. Prior to hospitalization these unmedicated patients were all in a residual state, had dropped out of psychiatric follow-up and had discontinued medication due to lack of compliance. Once psychotic symptoms re-occurred, these patients returned for treatment. Upon admission, a short-acting benzodiazepine was used when necessary to control agitation and restlessness until blood was collected, after which antipsychotic treatment was started. The remaining 25 schizophrenic patients were receiving at the time of the study various antipsychotic medications at conventional doses, including haloperidol (n=7), chlorpromazine (n=6), perphenazine (n=4), clozapine (n=6) and resperidone (n=2). Some received additional anticholinergic medications and benzodiazepines. Most of the patients were exposed to prolonged antipsychotic medication. MDD patients (n=17) received an antidepressant treatment, mostly selective serotonin reuptake inhibitors, or tricyclic antidepressants. BD patients (n=10), all depressed at the time of the study, were on a combination of a mood stabilizers and antidepressants. Patients who needed additional medications for other medical conditions were excluded. All patients were given an explanation of the purpose of the study and provided a written informed consent. The study was approved by the Institutional Review Board.

TABLE 1

Clinical data for the various groups

|  | Controls | Schizophrenic patients | | Depressed patients | |
|---|---|---|---|---|---|
|  |  | Medicated | Unmedicated | MDD | BP |
| No. of patients | 24 | 25 | 25 | 17 | 10 |
| Gender (F/M) | 13/11 | 10/15 | 14/11 | 11/6 | 6/4 |
| Age ± SD (range) | 35.0 ± 9.8 (22-50) | 25.9 ± 7.0 (18-43) | 32.0 ± 13.0 (18-60) | 53.0 ± 14.0[a] (33-75) | 50.0 ± 13.5[b] (27-75) |
| Duration of Illness (range) |  | 5.2 ± 5.5 (0.5-20) | 4.2 ± 10.0 (0.5-20) | 10.3 ± 10.3 (0.5-34) | 18.0 ± 11.1[c] (2-41) |

A significant difference for age and duration of illness was demonstratsd in depressed patients as compared with the schizophrenic or control groups, which did not differ from each other. The significance of the difference (df = 100 F = 19.291 p <0.0001 for age of subjects; df = 76 F = 6.720 p = 0.0005 for duration of illness) was analyzed by one way ANOVA followed by Bonferroni.
[a]$p < 0.001$ (t = 5.033);
[b]$p < 0.01$ (t = 3.533) vs. control,
[c]$p < 0.01$ (t = 5.367) vs. schizophrenic patients.

Isolation of Mitochondria from Platelets

Blood (40-80 ml) was collected from the cubital vein without tourniquet between 8:00 and 10:00 a.m., mixed 9:1 with 3.8% (w/v) tri-sodium citrate, and platelet-rich plasma (PRP) separated at room temperature by centrifugation at 200×g for 20 min. Platelets were isolated and washed with Tyrode's buffer pH 7.4 containing 1 mM EDTA as described previously (Krige et al., 1992). The platelet pellet was gently resuspended in ice cold 10 mM Tris buffer pH 7.4 containing 250 mM sucrose and 1 mM EDTA and disrupted by a Dounce A homogenizer (20-30 strokes). The breakdown of the platelets was verified by light microscopy. The homogenate was centrifuged at 1000×g at 4° C. for 20 min to remove unbroken cells. The supernatant, containing the cytoplasmic extract was centrifuged at 12,000×g at 4° C. for 15 min and an enriched mitochondrial fraction was isolated on percoll as described previously (Ben-Shachar et al., 1995; Gavin et al., 1990; McComark and Denton, 1989). Electron microscopy showed a sediment of intact mitochondria with dense granules and α-granules. The final preparation was immediately stored at −70° C. until use.

Mitochondrial Enzyme Activity

Mitochondrial respiratory chain enzymes activity was assayed blindly and in triplicate after two cycles of freezing and thawing in a final volume of 1 ml at 25° C. by standard techniques. Alternatively, 1% digitonin was added for 1 min and subsequently diluted 1:100 by the addition of the buffer before the start of the reaction. Briefly, complex I activity was assayed by two different methods using either ubiquinone (CoQ) or ferricyanide as electron acceptors.

NADH Ferricyanide Reductase Activity

NADH ferricyanide reductase activity was determined at $V_{max}$ ferricyanide throughout the study with or without antimycin A (Singer, 1974). Kinetic analysis was performed in mitochondrial preparation (0.25 mg protein/ml) at 25° C. in 50 mM Tris-HCl buffer pH 7.4 containing 0.25 M sucrose. Mitochondria were disrupted by pretreatment either by thawing and freezing, or with 1% digitonin for 1 min, subsequently diluted 1:100 by the addition of the buffer before the start of the reaction. There was no difference between both procedures. The reaction was started by the addition of 0.1 mM potassium ferricyanide and 0.14 mM, NADH. The decrease in NADH absorbance was followed at 340 nm for 1 min with a 3 sec interval between successive readings and 1 sec initial delay. In this mitochondrial preparation rotenone had no effect on NADH ferricyanide reductase activity.

NADH-CoQ Reductase Activity

NADH-CoQ reductase activity was assayed in 20 mM potassium-phosphate buffer pH 7.2 containing 5 mM $MgCl_2$ and 1 mM KCN. NADH 0.14 mM and 0.50 μM decylubiquinone (2,3-dimethoxy-5-methyl-6-decyl-1,4-benzoquinone) were added with or without 10 μM rotenone or 10 μg antimycin A as described previously (Estornell, 1993; Hatefi, 1978; Ragan et al., 1987). The residual activity of NADH CoQ reductase in the presence of rotenone was 5-15%.

Results from both assays for each sample are expressed as the difference between reductases activities in the absence and the presence of the relevant inhibitors.

For Dopamine inhibition studies, aliquots of samples were incubated with or without dopamine 10 exp (−5) M for one minute prior to initiation of the reaction. The level of activity of mitochondrial complex I was determined in the presence and absence of dopamine, using the methods described above.

Statistical Analysis

The results were analyzed according to standard statistical tests. Non-parametric descriptive statistics were used to avoid assuming a definite theoretical normal distribution of the data set. Parametric tests were performed to detect any difference between the various groups. Inter-group differences on the various dependent variables were assessed by one way ANOVA followed by Bonferroni post hoc multiple comparisons test. Linear regression analysis was used to estimate the relationship between NADH ferricyanide reductase and NADH CoQ reductase activities.

All chemicals for enzyme analyses were purchased from Sigma Chemical Co. St. Louis, Mo., USA. Protein concentration was measured using Biuret reaction.

Results

Correlation Between NADH Ferricyanide Reductase and NADH CoQ Reductase Activities Complex I activity can be measured by two methods, using either CoQ or the artificial electron acceptor ferricyanide. The assay using ferricyanide is the most reliable and sensitive measure of NADH dehydrogenase activity (Singer, 1974); it has the added advantage that it requires only half the amount of blood. A highly significant correlation ($p<0.001$, $r=0.85$) was found between NADH ferricyanide, reductase and NADH CoQ reductase activities in platelet mitochondria of 40 subjects from the various patients groups and healthy controls (not shown). Therefore, the rest of the study was carried out by measuring NADH ferricyanide reductase activity at $V_{max}$ ferricyanide.

NADH Ferricyanide Reductase Activity

Reference is now made to FIG. 1, which shows individual values of NADH ferricyanide reductase activity, which were markedly increased in mitochondrial preparation from platelets of schizophrenic patients in acute exacerbation compared with those from control subjects. In contrast, no difference in enzyme activity was observed between depressed patients with recurrent major depression, those with bipolar disorder and control subjects. Only a minimal overlap was observed between the individual values of schizophrenic patients and the remaining, groups. Quantitatively, one way ANOVA revealed a significant difference between the groups ($F=42.522$; $df=100$ $p<0.0001$). A set of Bonferroni, post hoc analyses showed that both the medicated and unmedicated schizophrenic groups were significantly different from controls ($t=5.5116$ and $t=4.790$ for medicated and unmedicated schizophrenics, respectively $p<0.001$). The schizophrenic subjects were also significantly different from both groups with affective disorders ($t>6.604$, $p<0.001$ for all interactions between the schizophrenic groups and the affective disorders groups). Table 2 summarizes the means±SD of all groups.

Age was significantly different between patients with affective disorders and the remaining groups. ANCOVA control for age did not change the significance of the difference between the schizophrenic patients and the patients with affective disorders and control subjects.

NADH ferricyanide reductase activity was analyzed in schizophrenic patients who did not receive medication for various periods (for at least one month, and most patients had not received medication for significantly longer periods, up to several years). No significant difference was observed between patients who were unmedicated for 1-3 months and those who had not received medication for more than a year prior to the study. Sixty percent of the unmedicated patients received upon admission a single administration of a short acting benzodiazepine to control agitation and restlessness until blood was collected. No significant difference ($t=0.08$, $p=0.9412$) was observed between the two groups. Thus, all unmedicated patients were pooled into one group. NADH ferricyanide reductase activity was similar in medicated and unmedicated schizophrenic patients.

The ability of Dopamine to inhibit NADH-ferricyanide reductase activity was investigated by pre-incubating samples from schizophrenic patients and from controls with dopamine prior to initiation of the enzyme assay. Dopamine inhibited NADH-ferricyanide reductase activity to a greater extent in schizophrenic patients compared with control subjects, subjects with major depression and subjects with bipolar disorder, as shown in Table 2.

TABLE 2

Mitochondrial NADH-ferricyanide reductase activity in platelets of schizophrenic patients, patients with affective disorders and control subjects.

| Subjects | NADH dehydrogenase activity (nmol/mg protein/min) | Dopamine inhibition (%) |
|---|---|---|
| Controls (n = 24) | 131.87 ± 53.1 | 38.6 ± 13.4 |
| Medicated schizophrenics (n = 25) | 319.60 ± 85.0* | 69.1 ± 19.9* |
| Unmedicated schizophrenics (n = 25) | 296.85 ± 54.7* | 72.6 ± 15.0* |
| Recurrent major depression (n = 17) | 136.21 ± 44.9 | 31.7 ± 16.5 |
| Bipolar disorder (n = 10) | 136.50 ± 57.7 | 34.5 ± 13.6 |

Values are means ± SD.
*$p < 0.001$ vs. controls and vs. both groups of depressed patients was analyzed by Bonferroni post hoc test.

A crucial factor in any diagnostic assay is the reproducibility of the results. The reproducibility of complex I activity measure is demonstrated in Table 3.

TABLE 3

Sample reproducibility of complex I activity in control subjects

| Number of subject | Number of sampling | Complex I activity (nmol/mg Protein/min.) |
|---|---|---|
| 1 | 4 | 199.28 ± 16.10 |
| 2 | 4 | 112.50 ± 16.10 |

TABLE 3-continued

Sample reproducibility of complex I activity in control subjects

| Number of subject | Number of sampling | Complex I activity (nmol/mg Protein/min.) |
|---|---|---|
| 3 | 2 | 167.14 ± 4.82 |
| 4 | 5 | 163.93 ± 15.43 |
| 5 | 3 | 72.32 ± 7.39 |
| 6 | 5 | 208.93 ± 19.28 |
| 7 | 2 | 159.11 ± 28.93 |
| 8 | 2 | 186.43 ± 4.02 |
| 9 | 3 | 393.75 ± 48.21 |

Intra-sample variation was determined by repeated measurements of complex I activity at various time points over a period of one year. Results are means ± SD.

NADH Ferricyanide Reductase Activity Normalized for Cytochrome c Oxidase Activity Cytochrome c oxidase was used as a marker for the estimation of mitochondrial mass and purity between samples.

To show that cytochrome c oxidase has similar activity in all groups, cytochrome c oxidase was assayed by following the decrease in the absorbance of reduced cytochrome c at 550 nm (Storrie and Madden, 1990).

Table 4 presents cytochrome c oxidase activity in platelet mitochondria from the various group. No statistically significant differences were found among the groups.

TABLE 4

Cytochrome c oxidase activity in mitochondria from platelets of schizophrenic patients, patients with affective disorders and control subjects.

| Subjects | Cytochrome c oxidase activity (nmol/mg protein/min) |
|---|---|
| Controls (n = 24) | 39.20 ± 15.87 |
| Medicated schizophrenics (n = 25) | 33.29 ± 17.70 |
| Unmedicated schizophrenics (n = 25) | 45.69 ± 24.83 |
| Major depression (n = 17) | 34.81 ± 15.23 |
| Bipolar disorder (n = 10) | 30.9 ± 12.91 |

Values are means ± SD. The number of patients is given in parentheses. No statistically significant difference was obtained.

Figure 2:
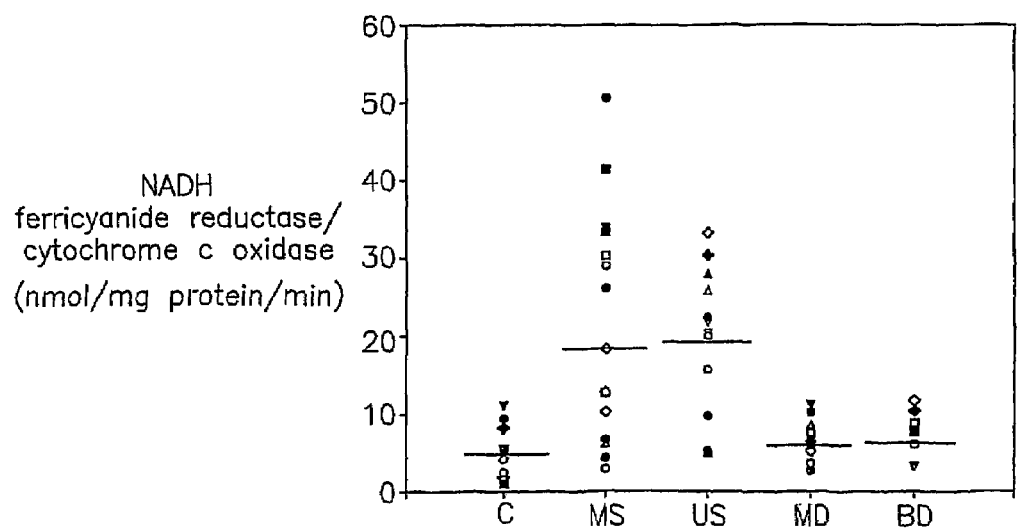
FIG. 2: depicts individual values of NADH ferricyanide reductase activity normalized for cytochrome c oxidase activity in medicated (MS) and unmedicated (US) schizophrenic patients, patients with major depression (MD), patients with bipolar disorder (BP), and control subjects (C).

Since cytochrome c oxidase showed similar activity in all groups, it was used as a marker for the estimation of mitochondrial mass and purity between samples. Reference is now made to FIG. 2, which shows NADH ferricyanide reductase activity normalized for cytochrome c oxidase activity. As shown in FIG. 2, normalization did not affect the previously described between-groups differences. Quantitatively, one way ANOVA revealed a significant difference among the groups (F=11.429; df=67 p<0.0001). A set of Bonferroni post hoc analyses showed that both schizophrenic groups were significantly different from the control group (t=4.951 and t=4.777 for medicated and unmedicated schizophrenic patients, respectively p<0.001). Both schizophrenic groups were significantly different from both groups of patients with affective disorders (t>3.714, p<0.01 in all cases). No significant difference was found in normalized complex I activity between medicated and unmedicated schizophrenic patients or between the two affective disorder group and control subjects.

Complex I Activity as a Function of Clinical State

Schizophrenic patients at various stages of the disease (patients at acute phase, residual patients with pronounced positive symptoms, and residual patients without pronounced positive symptoms who experience mainly negative symptoms) were recruited. Healthy control subjects were matched as much as possible for age and sex. All patients were formally diagnosed according to DSM-IV criteria and were evaluated by a senior psychiatrist using positive and negative symptom scale (PANSS). Complex I activity was significantly increased in both the acute patients and residual patients having pronounced positive symptoms as evaluated by PANNS, while patients in a residual state lacking pronounced positive symptoms showed a decrease in mitochondrial complex I activity (Table 5). A high correlation was found between most parameters of the positive category and complex I activity in the schizophrenic population (Table 6) with r=0.74; p<0.001 between total positive scores and activity. These results indicate that alteration in complex I activity is state dependent.

TABLE 5

Mitochondrial NADH frricyanide reductase (complex I) activity in platelets of schizophrenic patients at various disease stages.

| Subjects | Complex I activity (nmol/mg protein/min) |
|---|---|
| Controls (n = 48) | 218.23 ± 102.26 |
| Schizophrenics at acute phase (n = 56) | 419.96 ± 82.14*† |
| Chronic schizophrenics with positive symptoms (n = 22) | 402.23 ± 99.43*† |
| Chronic patients with residual schizophrenia (n = 23) | 115.84 ± 104.42** |

Values are means ± SD. The number of patients is given in parentheses.
*$p < 0.0001$,
**$p < 0.002$ vs. controls,
†$p < 0.0001$ vs. residual schizophrenia analyzed by Bonferroni post-hoc test.

TABLE 6

Pearson's correlation between complex I activity and clinical characteristics of 47 chronic schizophrenic patients

| Scale for assessment of positive symptoms | Pearson's correlation (r) | Significance (2-tailed) (p<) |
|---|---|---|
| delusion | 0.546 | 0.013 |
| hallucination | 0.53 | 0.016 |
| excitement | 0.513 | 0.021 |
| grandiosity | 0.715 | 0.0001 |
| suspiciousness | 0.608 | 0.004 |
| hostility | 0.741 | 0.0001 |
| All positive | 0.704 | 0.001 |
| General | 0.667 | 0.001 |
| Sum of symptoms | 0.455 | 0.044 |

Twenty schizophrenic patient were evaluated by using Positive and Negative Symptom Scale (PANSS) for schizophrenia. Ten showed pronounced positive symptoms and ten patients were in a residual state. Results show only the symptoms which showed significant correlation with complex I activity.

Example 2

Complex I Alteration is Expressed at the Level of Translation of its 24 and 51 kDA Subunit but not the 75 kDA Subunit Materials and Methods RT-PCR Analysis The expression of 24-, 51- and 75-kDa subunits of complex I in platelets was studied by using the RT-PCR technique. Total RNA was isolated using RNA STAT-60 kit (TEL-TEST, INC.). For cDNA synthesis and PCR amplification Reverse Transcriptase kit from Promega and FastStart kit from Roche Molecular Biochemicals were used. A single cDNA strand was synthesized by reverse transcriptase reaction. 5 μg of total RNA were incubated with 1 μg Random Primer at 70° C. for 5 min before the addition of 8 μl 5×MMLV, 20 mM dNTP mix, 24 units of RNasine and 400 units of MMLV Reverse Transcriptase. Double-distilled DEPC water was added to a final volume of 40 μl. The assay mixture was incubated at 37° C. for 1 hour and then at 95° C. for 5 min.

Amplification of ssDNA of the subunits was performed by PCR reaction. PCR incubation mixture contained 25 mM dNTP mix, 2.5 μl of 10×PCR buffer plus 20 mM $MgCl_2$, 5 mM $MgCl_2$, 5×GC-RICH solution, 1 unit of FastStart Taq DNA Polymerase, 10 pM 3' primer, 10 pM 5' primer and 1.5 μl of RT-product. Double-distilled water was added to a final volume of 25 μl. The mixture was incubated in a T3 Thermocycler with first denaturation at 95° C. for 5 min; the following denaturation at 95° C. for 1 min, annealing at 60° C. for 1 min, extension at 72° C. for 1 min, for 38 cycles of amplification with final extension at 72° C. for 10 min. The region amplified by PCR was between 120 and 760 bases forming a 641 bp fragment for 24 kDa; between 211 and 637 bases forming a 427 bp fragment for 51 kDa; between 1231 and 2230 bases forming a 1000 bp fragment for 75 kDa. RT-PCR products were assessed in a 2% agarose gel containing ethidium bromide. A 2645-36 bp DNA ladder (NOVEX) was used as a base pair reference marker. To control for the quality of RT-PCR assay and to prevent cross contamination, RNA extraction, RT-PCR assay set-up and post-RT-PCR product analysis were carried out separately. A parallel PCR reaction was performed with a pair of sense and antisense β-actin specific primers, for normalizing variations in RNA aliquots taken for RT reaction and gel loading.

Subjects

The total number of subjects assayed for mRNA levels:

| Subunit | Controls | Schizophrenic patients |
| --- | --- | --- |
| 24 kDa | 17 | 43 |
| 51 kDa | 19 | 31 |
| 75 kDa | 12 | 32 |

Results

Figure 3:
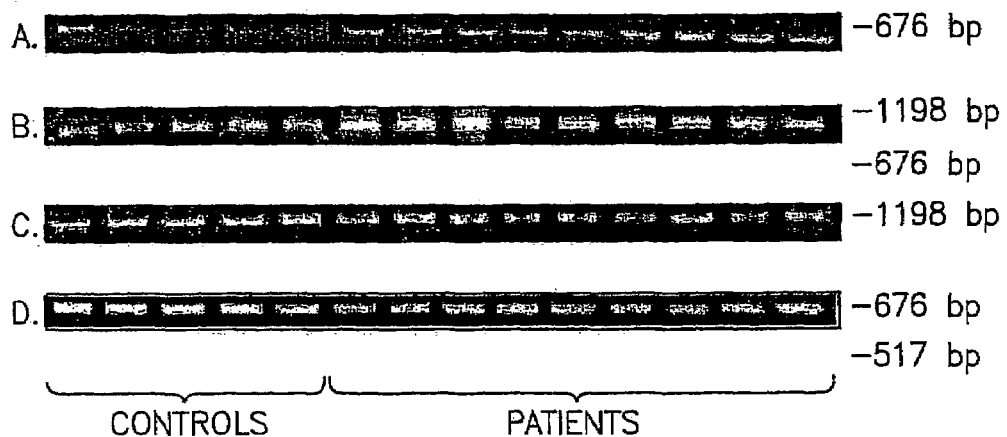
FIG. 3: is a photograph depicting RT-PCR analysis of mitochondiral complex I from platelets of schizophrenic patients and healthy control subjects.

Reference is now made to FIG. 3, which depicts RT-PCR analysis from platelets of schizophrenic patients at acute relapse and healthy control subjects. mRNA levels of 24 kDa subunit FIG. 3A) and 51 kDa subunit (FIG. 3B) of complex I, measured by RT-PCR, were higher in patients as compared with controls. Thus, the 24 kDa and 51 kDa subunit of complex I showed a similar alteration pattern to complex I activity in schizophrenic patients at acute relapse: and control subjects. In contrast, no change was found in the 75 kDa subunit (FIG. 3C). FIG. 3D depicts mRNA levels of β-actin, for normalizing variations in RNA aliquots taken for RT reaction and gel loading. Table 7 summarizes m-RNA levels of the 51 kDa subunit of mitochondrial complex I from several gels, normalized for beta-actin. Table 8 summarizes m-RNA levels of the 24 kDa subunit of mitochondrial complex I from several gels, normalized for beta-actin. The brackets indicate the number of samples for each gel.

TABLE 7

Summary of m-RNA levels of the 51 kDA subunit of mitochondrial complex I from several gels

| gel | patients | controls | ratio (patients/control) |
| --- | --- | --- | --- |
| 1 | 2.106 (4) | 0.798 (1) | 2.639 |
| 2 | 0.139 (4) | 0.087 (6) | 1.597 |
| 3 | 0.246 (5) | 0.183 (9) | 1.344 |
| 4 | 1.528 (5) | 1.681 (1) | 0.908 |
| 5 | 1.700 (5) | 1.379 (5) | 1.232 |
| 6 | 1.830 (12) | 1.030 (6) | 1.776 |
| 8 | 1.794 (1) | 0.897 (1) | 2.000 |
| 9 | 0.333 (2) | 0.162 (1) | 2.055 |

TABLE 8

Summary of m-RNA levels of the 24 kDA subunit of mitochondrial complex I from several gels

| gel | patients | controls | ratio (patients/control) |
| --- | --- | --- | --- |
| 1 | 0.66 (1) | 0.108 (1) | 6.111 |
| 2 | 1.62 (1) | 0.82 (2) | 1.976 |
| 3 | 1.48 (5) | 0.47 (1) | 3.148 |
| 4 | 0.09 (4) | 0.01 (3) | 9.000 |
| 5 | 0.09 (11) | 0.01 (6) | 9.000 |
| 6 | 3.20 (12) | 0.97 (6) | 3.299 |

Example 3

Complex I Alteration is Expressed at the Level of Protein of its 24 and 51 kDa Subunits Materials and Methods Western Blot Analysis Platelets were isolated from 20 ml blood, washed with Tyrode's buffer pH 7.4 containing 1 mM EDTA according to Krige et al. (1992) and centrifuged at 1000 g for 15 min at 4. Pellet was suspended in 10 mM Tris buffer pH 7.4 containing 250 mM sucrose, 0.5% NP40 and TM protease inhibitor cocktail. Samples were placed on ice for 1 hour with in between vortex (4-5 times). The suspension was centrifuged at 10,000 rpm for 5 min. The supernatant (100-120 μg total protein) was diluted 1:1 in electrophoresis sample buffer containing 20% (v/v) glycerol, 4% (w/v) SDS, 250 mM Tris-HCl, pH 6.8, 10% (v/v) 2-mercaptoethanol, 0.5 mg/ml bromophenol blue. The protein sample was separated on a SDS acrylamide gel (14% and 7.5% gel for 24 kDa and 51 kDa subunits, respectively) and transferred to a nitrocellulose membrane. Rat brain mitochondria were used as a positive control. Quality of transfer was assayed by Ponceau staining. The nonspecific binding sites were blocked with 5% (w/v) nonfat milk in 40 mM Tris-Saline buffer pH 8 containing 0.5% Tween 20 (T-TBS). The membranes were incubated at 4° C. overnight with primary antibody (anti sera for bovine complex 124 kDa/51 kDa, diluted 1:350 in T-TBS containing 2% BSA. The 24 kDa/51 kDa antisera was a gift from Y. Hatefi, Scrippts Institute of Research). The blots were washed 3-5 times with T-TBS at room temperature and incubated for 1 hour at room temperature with goat anti-rabbit IgG, diluted 1:10,000 in T-TBS. The blots were then developed with Amersham's ECL and exposed to XLS Kodak film for 20-30 sec.

Subjects

For protein level of 24 and 51 kDa, samples from 34 schizophrenic patients and 15 control subjects were assayed.

Results

Figure 4:
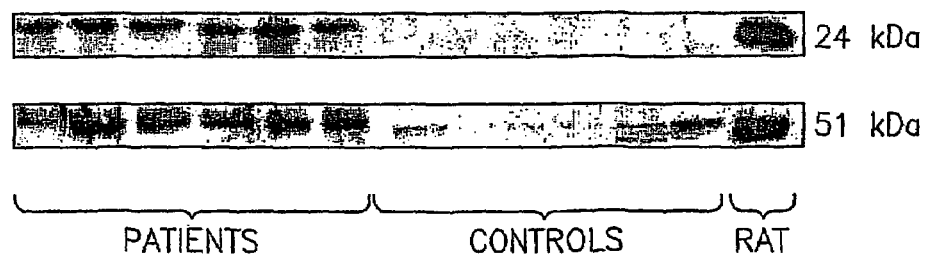
FIG. 4: is a photograph of ECL western blot analysis of the 24 and 51 kDa subunits of mitochondrial complex I in platelets of schizophrenic patients and healthy control subjects. Rat brain mitochondria are used as a positive control.

Reference is now made to FIG. 4, which is an ECL western blot analysis of the 24 kDa and 5.1 kDa subunits, of complex I in platelets of schizophrenic patients and healthy control subjects. As shown, protein levels were significantly increased in schizophrenic patients at acute relapse as compared to healthy subjects. Rat brain mitochondria were used as positive control.

It will be appreciated by persons skilled in the art that the present invention is not limited by what has been described hereinabove and that numerous modifications, all of which fall within the scope of the present invention, exist. Rather the scope of the invention is defined by the claims which follow:

REFERENCES

Attkisson C, Cook J, Karno M, et al. (1992) Clinical services research. Schizophr. Bull. 18. 561-626.

Barbeau D. Liang J J, Robitaille Y, Quirion R, Srivastava L K (1995). Decreased expression of yje embrionic form of the neuronal cell adhesion molecule in schizophrenic brains. Proc. Natl. Acad. Sci USA 92, 2785-2789.

Beal M F (1992). Does impairment of energy metabolism result in cytotoxic neuronal death in neurodegenerative illnesses? Ann. Neurol. 31, 119-130.

Ben-Shachar D, Zuk R, Gazawi H, Reshef A, Sheinkman A, Klein E (1999) Increased mitochondrial complex I activity in platelets of schizophrenic patients. Inter. J. Neuropsychopharmacol. 2, 245-253.

Ben-Shachar D, Zuk R, Glinka Y. (1995) Dopamine neurotoxicity: inhibition of mitochondrial respiration. J. Neurochem. 64, 718-723.

Bromet E, Harrow M, Kasl S (1974): Basic principles of epidemiologic research in schizophrenia. In: Handbook of Schizophrenia, vol. 3. Nosology, Epidemiology and Genetics of Schizophrenia. Tsuang M T, Simpson J C eds. Elsevier N.Y.

Burkhardt C, Kelly J P, Lim Y H, Filley C M, Parker W D (1993). Neuroleptic Medications inhibit complex I of the electron transport chain. *Annals of Neurology* 33, 512-517.

Cavalier L, Jazin E, Eriksson I, Prince J, Bave B, Oreland L, Gyllensten U (1995). Decreased cytochrome c oxidase activity and lack of age related accumulation of mtDNA in brain of schizophrenics. Genomics 29, 217-228.

Cohen G. Farooqui R, Kesler N. (1997). Parkson's Disease: A new link between monoamine oxidase and mitochondrial electron flow. Proc. Nat. Acad. Sci. USA 94, 4890-4894.

Da Prada M, Cesura A M, Launany J M, Richards J C (1988). Platelets, as a model for neurons? Experientia 44, 115-126.

Davis K L, Kann R S, Ko G, Davidson M (1991). Dopamine in schizophrenia: a review and reconceptualization. American Journal of Psychiatry 148, 1474-1486.

Dingman C W, McGlashan T H (1986) Discriminating characteristics of suicides: Chestnut Lodge follow-up sample including patients with affective disorders, schizophrenia and schizo-affective disorder. Acta Psychiatr. Scand. 74, 91-97.

Docherty N M, DeRosa M, Andreasen N C, (1996) Communication disturbances in schizophrenia and mania. Arch. Gen. Psychiatry 53, 358-364.

DSM-IV American Psychiatric Association: Diagnostic and Statistical Manual of Mental disorders, 4th ed (DSM-IV). Washington, D.C., APA, 19.

Estornell E, Fato R, Pallotti F, Lenaz G (1993). Assay conditions for the mitochondrial NADH:coenzyme Q oxidoreductase. *FEBS* 332, 127-131.

Ganguli R, Brar J S, Chengappa K N, Yang Z W, Nimgaonkar V L, Rabin B S (1993) Ann. Med. 25, 489-496.

Gavin C E, Gunter K K, Gunter T E (1990). Manganese and calcium efflux kinetics in brain mitochondria, relevance to manganese toxicity. Biochemical Journal 266, 329-334.

Gur R E, Resnick S M, Alavi A, Gur R C, Caroff S. Dann R, Silver F L, Saykin A J, Chwluk J B, Kudhner M. (1987). Regional brain function in schizophrenia II: repeated evaluation with positron emission tomography. Arch. Gen. Psychiatry 44, 126-129.

Harlow and Lane, Antibodies: A Laboratory Manual, (Cold Spring Harbor Laboratory, Cold Spring Harbor, N.Y.), 1988.

Hatefi Y (1978). Preparation and properties of the enzyme complexes of the mitochondrial oxidative phosphorylation system. *Methods in Enzymology* 53, 3-10.

Hietala J, Syvalahti E. (1996) Dopamine in schizophrenia. Ann Med 28, 557-61.

Kaiya H (1992) Second messenger imbalance hypothesis of schizophrenia. Prostaglandins Leukotriens & Essential Fatty Acids 46, 33-38.

Krige D, Carroll M, Cooper J M, Maesden C D, Schapira A H V (1992). Platelet mitochondrial function in Parkinson's disease. Annals of Neurology 32, 782-788.

Kung L, Roberts R C (1999) Mitochondrial pathology in human schizophrenic striatum: a postmortem ultrastructural study. Synapse 31, 67-75.

McComark J G, Denton R M (1989). Influence of calcium ion on mammalian intramitochondrial dehydrogenases. Methods in Enzymology 174, 95-118.

McGlashan T H, (1988) A selective review of recent North American long-term follow-up studies of schizophrenia. Scizophr. Bull. 14, 515-542.

McGlashan T H, Fenton W S (1992) The positive/negative distinction in schizophrenia: review of natural history validators. Arch. Gen. Psychiatry 49, 63-72.

Parker W D, Filley C M, Parks J K (1990). Cytochrome oxidase deficiency in Alzheimer's disease. Neurology 40, 1302-1303.

Prince J A, Blennow K Gottfies C G, Karlsson I Oreland L (1999) Mitochondrial function is differentially altered in the basal ganglia of chronic schizophrenics. Neuropsychopharmacol. 21, 372-379.

Przedborski S, Jackson-Lewis V, Muthane U, Jiang H, Ferreria M, Naini A B, Fahn S (1993). Chronic levodopa administration alters cerebral mitochondrial respiratory chain activity. Ann. Neurol. 34, 715-723.

Raedler T J, Knable M B, Weinberger D R (1998) Current Opinion in Neurobiol. 8, 157-161.

Ragan C I, Wilson M T, Darley-Usmar V M, Lowe P N (1987). Subfractionation of mitochondria and isolation of the proteins of oxidative phosphorylation. In: Darely-Usmar, V. M., Rickwood, D. and Wilson, M. (Eds.), Mitochondria, a Practical Approach (pp. 79-112). London: IRL Press.

Rosental R E, Hamud F, Fiskum G, Vrghese P J, Sharpe S (1987) Cerebral ischemia and reperfusion: prevention of brain mitochondrial injury by lidoflazine. J. Cereb. Blood Flow Metab. 7, 752-758.

Schapira A H V, Cooper J M, Dexter D (1990). Mitochondrial complex I deficiency in Parkinson's disease. J. Neurochem. 54, 823-827.

Schroder Holcomb H H, Cascella N G, Thaker G K, Medoff D R, Dannals R F, Tamminga C A (1996). Functional sites of neuroleptic drug action in the human brain: PET/FDG studies with and without haloperidol. Am. J. Psychiatry 153, 41-49.

Seeman P. (1987). Dopamine receptors and the dopamine hypothesis of schizophrenia. Synapse 1, 133-152.

Sheitman B B., Lee H., Strauss R. Lieberman J A. (1997) The evaluation and treatment of first-episode psychosis. Schizophrenia Bull 23, 653-61.

Singer T P (1974). Determination of the activity of succinate, NADH, Choline and glycerophosphate dehydrogenases. In: Glick, E. (Ed.), Methods of Biochemical Analysis. Vol. 22 (pp. 123-175). New York: International Science.

Storrie B, Madden E A (1990). Isolation of subcellular organelles. Methods in Enzymol. 182, 203-225.

Strunecka A., Ripova D, (1999) What can the investigation of phosphoinositide signaling system in platelets of schizophrenic patients tell us? Prostaglandins Leukotriens & Essential Fatty Acids 61, 1-5.

Takahashi Y (1954). All enzymological study on brain tissue of schizophrenic patients. Carbohydrate metabolism. Folia Psychiatrica Neurologica Japonica 7, 214-237.

Tamminga C A, Thaker G K, Buchanan R, Kirkpatrick B, Alphs L D, Chase T N, Carpenter W T (1992). Limbic system abnormalities identified in schizophrenia using positron emission tomography with fluorodeoxyglucose and neocortical alterations with deficit syndrome. Arch. Gen. Psychiatry 49, 522-530.

Tsuang M T, (1978) Suicide in schizophrenics, manics, depressives and surgical controls: a comparison with general population suicide mortaliy. Arch. Gen Psychiatry 35, 153-155.

Uranova N A, Aganova E A (1989). Ultrastructure of synapses of the anterior limbic cortex in schizophrenia. Zhurnal Nevropatologii I Psikhiatrii Imeni S-S-Korsakova. 89, 56-59.

Whatley S A, Curi D, Das Gupta F, Ferrier I N, Jones S., Taylor C, Marchbanks R M (1998). Superoxide, neuroleptics and the ubiquinone and cytochrome b5 reductases in brain and lymphocytes from normals and schizophrenic patients. Mol. Psychiatry 3, 227-237.

Whatley S A, Curi D, Marchbanks R M (1996). Mitochondrial involvement in schizophrenia and other functional psychoses. Neuroch. Res. 21, 995-1004.

Willner P (1997) The dopamine hypothesis of schizophrenia: current status, future prospects. Int Clin Psychopharmacol 12, 297-308.

Wirz-Justce A (1988). Platelet research in psychiatry. Experientia 44, 152-155.

Wyatt R J, Henter I, Leary M C, Taylor E (1995) An economic evaluation of schizophrenia-1991. Soc. Psychiatry Psychiatr. Epidemiol. 30, 196-205.

Yao J K, van Kammen D P (1996) Incoporation of 3H-arachidonic acid into platlet phospholipids of patients with schizophrenia Prostaglandins Leukotriens & Essential Fatty Acids 55, 21-26.

What is claimed is:

1. A method for diagnosing the clinical state of schizophrenia in a subject, said method comprising the steps of: obtaining a sample, wherein said sample is isolated mitochondria from either a mammalian blood, or a muscle tissue from the subject; determining the level of activity of the mitochondrial complex I enzyme in said sample; and comparing said level of activity wish a normative value of activity of mitochondrial complex I enzyme; wherein an increase in mitochondrial complex I enzyme activity in said sample compared with said normative value is indicative of the subject having schizophrenia at an acute phase or a residual phase with pronounced positive symptoms and a decrease in mitochondrial complex I enzyme activity in said sample compared with said normative value is indicative of the subject having schizophrenia at a residual phase with pronounced negative symptoms.

2. The method according to claim 1, wherein said sample is isolated mitochondria from a blood sample.

3. The method according to claim 2, wherein said blood sample is a platelet, lymphocyte, leukocyte, monocyte, or T-cell, B-cell or neutrophil blood sample.

4. The method according to claim 1, wherein said blood sample is enriched for mitochondria.

5. The method according to claim 2, wherein said blood sample is a platelet sample.

6. The method according to claim 5, wherein said platelet sample is enriched for mitochondria.

7. The method according to claim 1, wherein the level of activity of said mitochondrial complex I enzyme is determined by: adding a portion of said sample to a medium containing an electron acceptor, and NADH; and monitoring the change in absorbance of NADH.

8. The method according to claim 7, wherein said absorbance of NADH is measured for 1 minute at 3 second intervals.

9. The method according to claim 7, wherein said electron acceptor is ubiquinone.

10. The method according to claim 7, wherein said electron acceptor is ferricyanide.

11. A method for diagnosing schizophrenia in a subject, said method comprising the steps of: obtaining a sample from the subject; wherein said sample is isolated mitochondria from either a mammalian blood, or a muscle tissue; aliquoting two test samples; adding an inhibitor of mitochondrial complex I enzyme to the one of the test samples and determining the level of activity of a mitochondrial complex I enzyme in the two test samples so as to determine the level of inhibition; determining said level of inhibition as percentage of value of MCI activity, which is the activity inhibited by rotenone or antymycin A; wherein an altered inhibition and activity of mitochondrial complex I enzyme compared with a normative value of a control is indicative of the subject having schizophrenia.

12. The method according to claim 11, wherein said inhibitor is a catechol.

13. The method according to claim 11, wherein said inhibitor is dopamine, norepinephrine, 6-hydroxydopamine, L-DOPA or any combination thereof.

14. The method according to claim 11, wherein said inhibitor is dopamine.

15. The method according to claim 11, wherein said sample is isolated mitochondria from a blood sample.

16. The method according to claim 15, wherein said blood sample is a platelet, lymphocyte, leukocyte, monocyte, or T-cell, B-cell or neutrophil blood sample.

17. The method according to claim 15, wherein said blood sample is enriched for mitochondria.

18. The method according to claim 15, wherein said blood sample is a platelet sample.

19. The method according to claim 18, wherein said platelet sample is enriched for mitochondria.

20. The method according to claim 11, wherein a higher inhibition of mitochondrial complex I enzyme in said sample compared with said normative value is indicative of the subject having schizophrenia.

21. The method according to claim 11, wherein the level of activity of said mitochondrial complex I enzyme is determined by: adding a portion of said sample to a medium containing an electron acceptor and NADH; and monitoring the change in absorbance of NADH.

22. The method according to claim 21, wherein said absorbance of NADH is measured for 1 minute at 3 second intervals.

23. The method according to claim 21, wherein said electron acceptor is ubiquinone.

24. The method according to claim 21, wherein said electron acceptor is ferricyanide.

* * * * *